United States Patent [19]

Schneiderman

[11] 4,092,986

[45] June 6, 1978

[54] CONSTANT OUTPUT ELECTROSURGICAL UNIT

[75] Inventor: Max Schneiderman, Clifton, N.J.

[73] Assignee: Ipco Hospital Supply Corporation (Whaledent International Division), New York, N.Y.

[21] Appl. No.: 695,525

[22] Filed: Jun. 14, 1976

[51] Int. Cl.² .................... A61B 17/36; A61N 3/00
[52] U.S. Cl. .................. 128/303.14; 128/303.17; 128/422; 330/107; 331/183
[58] Field of Search .............. 128/303.14, 303.17, 128/303.18, 303.13, 422; 330/107; 331/183

[56] References Cited

U.S. PATENT DOCUMENTS

| 2,993,178 | 7/1961 | Burger | 128/303.14 X |
| 3,284,724 | 11/1966 | Marlow | 331/183 X |
| 3,512,102 | 5/1970 | Kubach | 330/107 |
| 3,730,188 | 5/1973 | Ellman | 128/303.14 |
| 3,875,945 | 4/1975 | Friedman | 128/303.14 |
| 3,964,487 | 6/1976 | Judson | 128/303.14 |
| 4,032,860 | 6/1977 | LeVeen | 331/183 X |

FOREIGN PATENT DOCUMENTS 1,347,865   11/1963   France ........................... 128/303.14

Primary Examiner—Robert W. Michell
Assistant Examiner—Lee S. Cohen
Attorney, Agent, or Firm—Friedman, Goodman & Teitelbaum

[57] ABSTRACT

An electrosurgical unit which provides a voltage output to a load. An oscillator in the unit produces the output of a given frequency. A switching circuit coupled to the oscillator provides an unmodulated RF carrier from the oscillator for use in cutting procedures and a pulse modulated RF voltage from the oscillator for use in coagulation procedures. A feedback circuit is coupled from the output to the input of the oscillator to maintain the output voltage level from the unit at a substantially constant value independent of the load.

17 Claims, 6 Drawing Figures

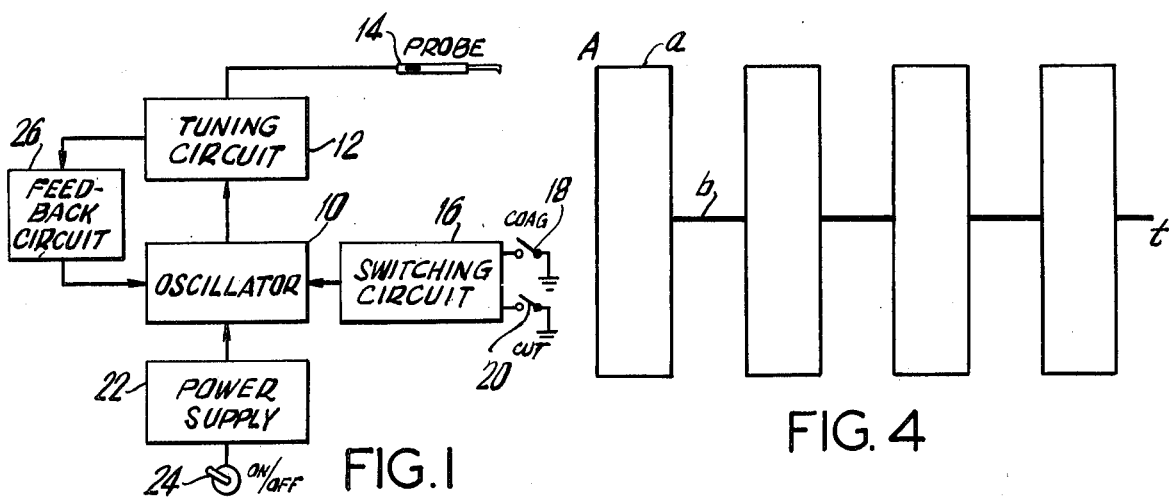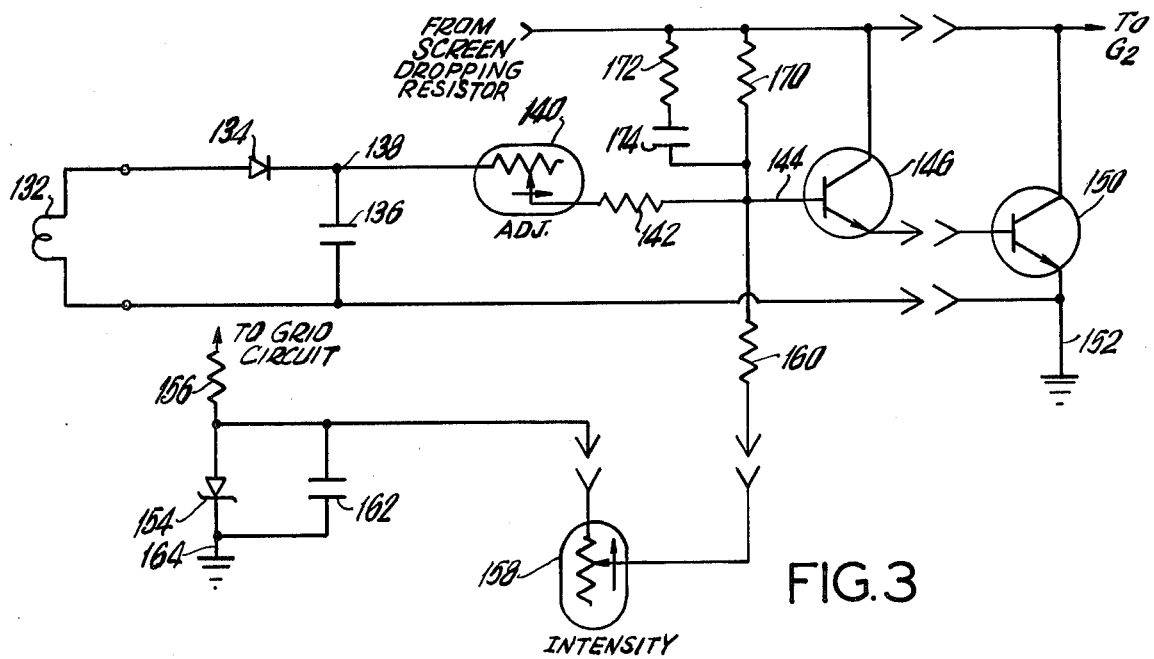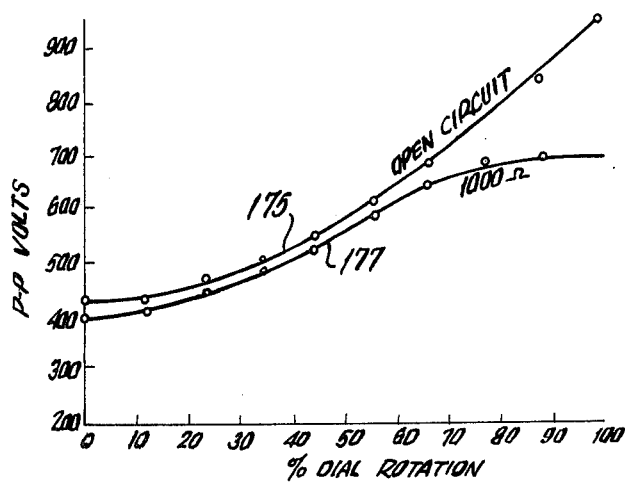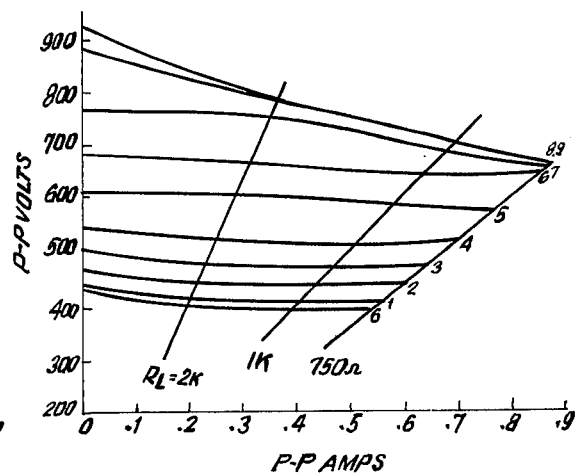

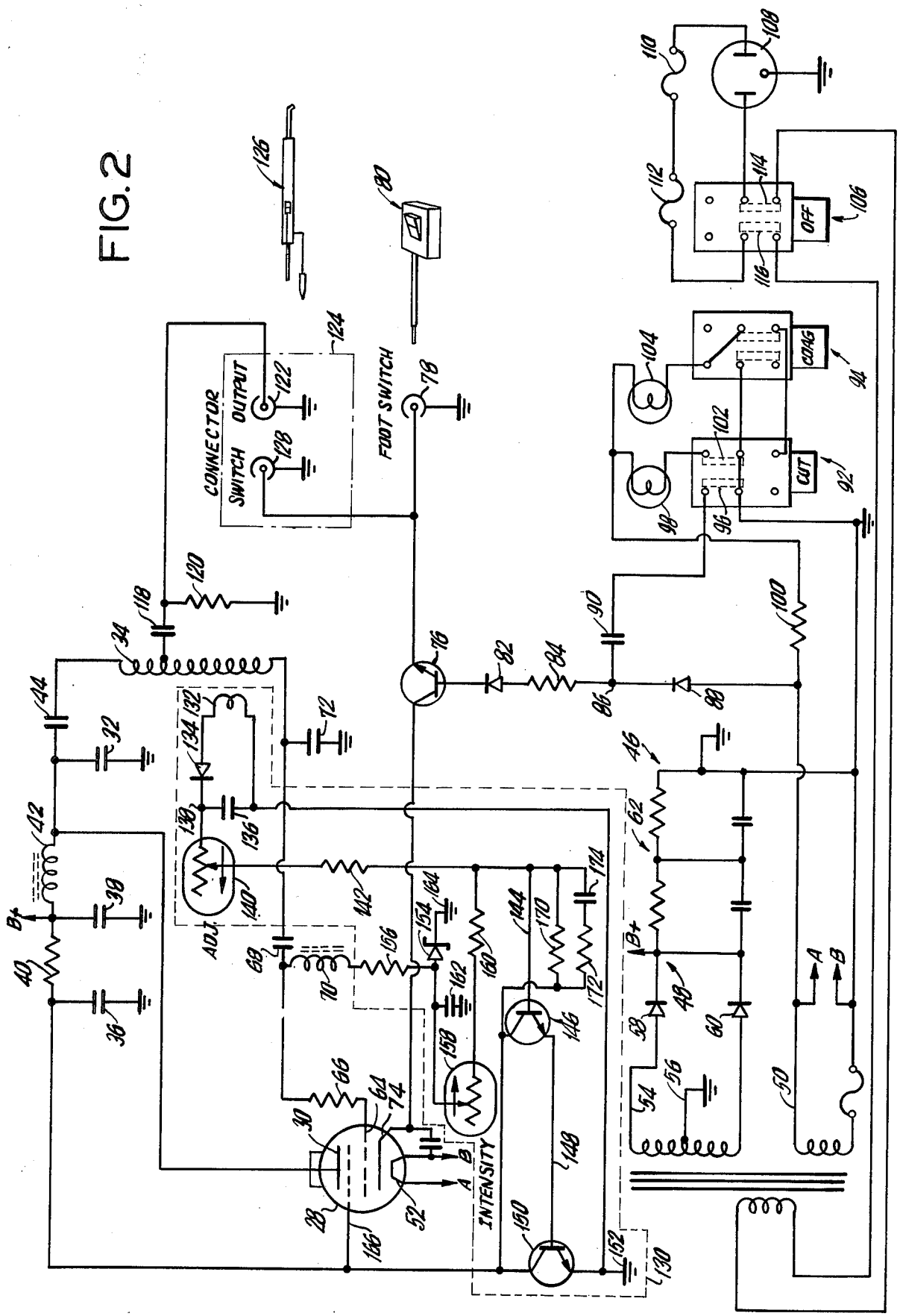

4,092,986

CONSTANT OUTPUT ELECTROSURGICAL UNIT

BACKGROUND OF THE INVENTION

This invention relates to electrosurgical units, and more particularly to such units with a continuously controllable output voltage whose level remains at a substantially constant value independent of the load.

It has been found that tissue cutting can be accomplished by applying an unmodulated RF carrier to a patient, while coagulation of blood vessels can be achieved by utilizing pulse modulated RF voltage signal. To achieve such electrical signals, there are presently available electrosurgical units which generally provide both an unmodulated and a modulated output voltage, which may be selectively used for tissue cutting or tissue coagulation. The amplitude of the output level of the voltage desired for a cutting or a coagulation procedure varies depending upon the depth of cut, the impedance provided by the patient, and numerous other factors relating to the electrode shape, environment and the particular operating procedure. Accordingly, it is necessary to provide some type of an intensity control whereby the amplitude of the output signal can be controlled. In some electrosurgical units, such intensity control is available only in discrete steps. The electrosurgical unit contains an oscillator with an output tank circuit, and connected to the tank circuit are a number of taps with a rotating dial switch connectable to the individual taps. The voltage level is selected by placing the dial at an appropriate tap. However, because of the many variations in the operating procedures, such discrete steps may not provide sufficient accuracy of control and may cause unwanted problems during its use. A further problem with existing electrosurgical units concerns maintaining the selected output desired. By using the intensity control, the particular output level can be selected for the cutting or coagulation procedure. However, once the output voltage is applied to the patient by means of a hand piece such as a probe or forceps, the patient acts as a load across the output of the electrosurgical unit which causes the output voltage level to drop. Such drops have provided great changes in the desired output level and often necessitate the operator to continuously reset the voltage level as the procedure is carried out. It therefore required the surgeon himself, or an associate, continuously monitor the voltage output level of the electrosurgical unit and continuously make appropriate adjustments as the load on the unit changes. This monitoring requires extra time and skill, and frequently may require the availability of an additional nurse or attendant. Should the voltage output not be monitored, the large variations in the voltage output can cause possible damage or harm to the patient by providing excessive depth of cutting or an improper amount of coagulation.

SUMMARY OF THE INVENTION

It is therefore an object of the present invention to provide an electrosurgical unit which avoids the aforementioned problems of prior art devices.

It is another object of the present invention to provide an electrosurgical unit with a substantially constant output voltage level which is independent of the load.

Yet a further object of the present invention is to provide an electrosurgical unit which provides a continuously adjustable output voltage level for both cutting procedures and coagulation procedures.

Still a further object of the present invention is to provide an electrosurgical unit which produces an unmodulated RF carrier for use in cutting procedures and a pulse modulated RF voltage for use in coagulation procedures, and wherein the output voltage level can be preset and maintained at a substantially constant value independent of the load.

Another object of the present invention is to provide an electrosurgical unit which provides a high ratio of peak to average voltage output thereby providing a great amount of discrimination between the cutting and the coagulation voltages.

A further object of the present invention is to provide an electrosurgical unit which contains a low source impedance, and utilizes inverse feedback to maintain a substantially constant voltage independent of the load.

These objects are achieved in accordance with a preferred embodiment of the present invention wherein there is provided an electrosurgical unit producing an output voltage to a load, and including an oscillator producing an output signal at a given frequency. A switching circuit is coupled to the oscillator for providing an unmodulated RF carrier voltage from the oscillator for use in cutting procedures and a pulse modulated RF voltage from the oscillator for use in coagulation procedures. A feedback circuit is coupled from the output to the input of the oscillator to maintain the selected output voltage level from the unit at a substantially constant value independent of the load.

In order to control the output voltage level, the feedback circuit includes a sampling means coupled to the oscillator output for providing a signal proportional to the output voltage. A control circuit is coupled to the oscillator and responds to the proportional signal for changing the voltage produced by the oscillator in a direction opposite to any change in the proportional signal.

The control circuit includes an amplifier means having its control electrode connected to receive the proportional signal and its output electrode connected to control the oscillator. An intensity control means is interconnected to the control electrode for determining the output level from the unit. This provides a continuously variable output voltage level.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is a block diagram of the electrosurgical unit of the present invention;

FIG. 2 is a detailed circuit diagram of the electrosurgical unit of the present invention;

FIG. 3 is a circuit diagram showing the feedback circuit alone;

FIG. 4 is a graph useful in explaining the operation of the electrosurgical unit of the present invention; and FIGS. 5 and 6 represent graphs showing results obtained by the use of electrosurgical units in accordance with the present invention.

DESCRIPTION OF THE PREFERRED EMBODIMENT

Referring now to FIG. 1, there is shown a block diagram of an electrosurgical unit and including an oscillator 10 which provides a high frequency output electrosurgical signal whose frequency is controlled by a tuning circuit 12. The output appears across the tuning circuit and is applied through a probe 14 to a patient. The type of output produced is controlled by a switching circuit 16. When a coagulation switch 18 is closed, the switching circuit controls the oscillator to produce a pulse modulated RF voltage. When the cutting switch 20 is closed, the switching circuit controls the output of the oscillator to provide an unmodulated RF output voltage for use in cutting procedures. A power supply 22 energizes the oscillator and is controlled by a main ON/OFF switch 24.

Electrosurgical units of the type thus described, are available. The level of output voltage is controlled at the tuning circuit, and in some cases by a series of discrete output steps. When the output voltage is applied to a load, such as a patient, the output voltage is reduced by the loading, whereby the intensity control must be adjusted in order to again produce the desired output voltage level. To alleviate the constant adjustments, the present invention includes a feedback circuit 26 coupled between the tuning circuit 12 and the oscillator 10. The feedback circuit monitors the output voltage produced at the tuning circuit, and when such voltage increases, the feedback circuit controls the oscillator to reduce its output. Similarly, when the output level decreases, the feedback circuit monitors such a decrease and causes the oscillator to produce a higher output voltage to counteract such a decrease. Therefore, the feedback circuit insures that the output voltage level from the unit will be a substantially constant value independent of the load. Such constant value is the desired level when using an unmodulated RF carrier voltage in cutting procedures, and is the average or peak to peak voltage when using a pulse modulated RF output voltage in coagulation procedures.

Referring now to FIG. 2, there is shown in more detail the circuit heretofore described. The oscillator is of the well known Clapp oscillator type and includes the vacuum tube 28 having its plate 30 connected across a tank output including a tuning capacitor 32 and a tank coil 34. The output is tapped off from the tank coil 34. Included in the plate and screen grid circuits are the bypass capacitors 36, 38 and the screen dropping resistor 40. An RF choke 42 isolates the tank coil from the power source. A blocking capacitor 44 is also included in the tank circuit. The plate is energized by means of the voltage supplied from the power supply, shown generally at the bottom by the circuit at 46. The power supply includes a full wave rectifier shown generally at 48, including a transformer having a secondary 50 which supplies a voltage at the points A-B to the filament 52 of the oscillator tube 28. Another secondary 54 has its center tapped at 56 and connected to ground. Current from secondary 54 passes through the diodes 58, 60 of a rectifier 48 and through the series of RC filters shown generally at 62. The B+ is taken across the filter network 62.

The control grid 64 of the tube 28 is connected to the parasitic suppressor resistor 66 which is in turn connected to the lower end of the tank coil 34 through the grid blocking capacitor 68. An RF choke 70 is also connected in series with grid resistor 156 across the grid output. Capacitor 72 couples the tank circuit to ground. The capacitor 72 is generally comprises of a number of capacitors placed in parallel in order to supply a sufficient amount of capacitance as is indeed with a safe RF current rating.

Connected to the cathode 74 of the oscillator tube 28 is a switching transistor 76. The collector-emitter path of the switching transistor 76 interconnects the cathode to ground through a foot switch control connected through socket 78. When a foot switch shown generally at 80 is interconnected into the foot switch socket 78 it permits interconnecting of the emitter to ground thereby causing the oscillator to operate. When the foot switch disconnects the emitter from ground, the oscillator stops producing its output voltage.

The base of the transistor 76 is connected through a diode 82 and a resistor 84 to junction 86 which prevents excessive current through the switching transistor 76 thus protecting it against breakdown. Connected to junction 86 is a rectifier diode 88 which is fed a fixed AC voltage taken from the secondary 50 of the transformer. Connected in parallel thereto is one terminal of capacitor 90. When the other terminal of the capacitor 90 is grounded, it acts as a filter capacitor applying a fixed DC voltage to the base of transistor 76 and causing an unmodulated RF voltage to be produced from the oscillator 28. The unmodulated voltage will appear across the oscillator tank circuit coil 34. When the capacitor 90 has its other end free and ungrounded, it is no longer included in the base circuit thus causing a pulsed voltage to be applied to base of transistor 76 and the oscillator 28 will produce a pulse modulated RF output signal.

It is to be noted that the pulse modulator RF output signal produced for coagulation procedures is an improved signal. Generally, a modulated signal will follow a sine wave curve where the output intensity increases to a maximum and then immediately decreases to a minimum and immediately begins increasing again. However, the present oscillator output is one which has pulses separated by "off" periods. Such output pulse is shown in FIG. 4 where it can be seen that it includes an "on" pulse a followed by an "off" pulse "b". Because of the On-Off pulsing, the ratio of peak to average power is high. Therefore, the difference between the coagulation voltage shown in FIG. 4 and a fixed cutting voltage is sufficiently large to produce enough discrimination to provide an improved coagulation signal.

Referring back to FIG. 2, the selection of the cutting or coagulation output is achieved by means of the switches 92 and 94. When the switch 92 is actuated by being pushed in, the capacitor 90 is interconnected to ground through the switch bar 96. At the same time, the indicator bulb 98 is connected in series with resistor 100 to ground via the switch bar 102, thereby illuminating the bulb 98. With the cut switch thus actuated, and the indicator bulb "98" "on", the capacitor is connected in the circuit and will cause an unmodulated RF carrier output from the oscillator.

To provide a coagulation output, the coagulation switch 94 is actuated by being pressed in. The bulb 104 will then be interconnected to ground, and at the same time the capacitor 90 will be disconnected from ground. The two switches 92 and 94 are mechanically interconnected so that actuation of one will release the other.

The main power switch 106 interconnects a plug 108 to the transformer primary through the fuses 110 and 112. Depressing the switch 106 will disconnect the circuit. However, when either the coagulation or the cut switches 92, 94 are actuated, they will automatically cause the switch 106 to be pushed out thereby interconnecting the plug across the bars 114, 116 and energizing the system.

The output from the tank coil 34 is taken via a blocking capacitor 118 and is shunted by a high resistance 120. The resistance 120 prevents any high transients from occurring across the output resulting from initial activation of the system. The output is then fed to an output socket 122 on a connector block 124. A probe 126 can be inserted into the output socket 122 thereby causing the output to appear across the end of the probe.

A switch socket 128, similar to the foot switch socket 78, can be placed in parallel with the foot switch and is also available on the connector block 124. A plug available on the probe 126 can be inserted into the socket 128 so that the oscillator can be activated either by the foot pedal 80 or the hand switch directly on the probe 126.

In the prior art, a series of taps would be connected across the coil 34 of the tank circuit and a moveable contact arm is selectively connected to the taps thereby providing an output intensity control at discrete tap values. However, the taps do not provide sufficient flexibility of control. Additionally, when a load is connected across the tank coil, the voltage drops and the change has to be monitored and corrected. Accordingly, in the present invention there is provided a feedback circuit connected between the output tank coil and the screen of the oscillator. An intensity control is included within the feedback circuit to provide a continuously variable output voltage rather than just discrete values.

The feedback circuit is shown contained within the dotted lines 130 shown in FIG. 2, as well as being shown as a separate circuit in FIG. 3. Inductively coupled to the tank coil 34 is a sampling circuit including the single turn coil 132. The voltage which appears across the output tank coil 34 induces a proportional voltage across the sampling loop 132. This voltage is then converted to a DC value by means of the detector, including the diode 134 and the capacitor 136. Therefore, the DC value appearing at the point 138 will be at a DC level proportional to the output voltage appearing across the tank coil 34, which in turn represents the output voltage of the electrosurgical unit. The DC voltage is fed across an adjustable resistor 140, and a fixed resistor 142 to the base 144 of the transistor 146. This transistor forms part of a Darlington amplifier by having its emitter connected to the base 148 of a second transistor 150. The other end of the coil 132 and the capacitor 136 is connected to ground at 152.

Also applied to the base 144 of the transistor 146 is a fixed voltage which is maintained at a predetermined DC value by means of the Zener diode 154. The Zener diode is connected through the resistor 156 to the choke 70 of the grid circuit. The fixed voltage across the Zener diode 154 is fed through an adjustable resistor 158 and a fixed resistor 160 to the base 144 of the transistor 146. A capacitor 162 is placed in parallel across the Zener diode 154 and the other end of the Zener diode is connected to ground at 164.

The emitter of transistor 150 is connected to ground 152, while the collector is connected to the screen 166 of the oscillator tube 28. The other end of the screen is connected via screen dropping resistor 40 to the B+ through line 168.

A resistor 170 is connected between the base and collector of the transistor 146 to provide inverse feedback on the transistor 146 itself. This keeps the voltage at the collector at a safe point within the collector-emitter rating of the transistor. A resistor-capacitor combination 172, 174 is also connected between the base and collector of the transistor 146 and serves as a stabilizing network. It introduces bandwidth shaping and prevents oscillations from occurring within the feedback loop.

The operation of the feedback circuit within the electrosurgical unit will now be explained. Generally the output voltage of the oscillator tube is controlled by the amount of voltage on the screen of the tube. When a given amount of output voltage appears at the tank coil 34, its value is sampled by the coil turn 132 which provides a DC level which is added to the predetermined fixed level determined by the Zener 154, and feeds the base 144 of the transistor 146. This in turn feeds the transistor 150 which is connected to the screen 166. When a load is placed across the output voltage, there is tendency for the output voltage to lower. The voltage across the sampling coil 132 would also decrease, which will decrease the voltage level at the base 144 of the transistor 146. This also decreases the base voltage of the transistor 150. As the result, the transistor 150 is not driven as hard and takes less current through it. Therefore, more current is provided to the screen which increases its voltage and thereby causes the oscillator to produce a higher voltage. This higher voltage counteracts the decrease caused by the load and tends to maintain the output voltage constant.

Should the output voltage increase, this increment would also be sampled by the coil 132 which will then increase the drive to the base 144 of the transistor 146, which in turn would drive the transistor 150 harder, causing more current through the transistor 150 and causing the voltage at the screen 166 to be lowered thereby reducing the output voltage.

It will therefore be seen that the use of the feedback circuit feeds the oscillator in a direction opposite to the change in output voltage produced by the electrosurgical unit when a load is placed on the unit. The feedback circuit also acts to maintain the output constant regardless of changes in primary input voltage from the AC mains.

The adjustable resistor 140 provides an internal adjustment to account for initial tolerance variations in the system. This can be adjusted by the factory prior to shipment by means of a screw driver. To adjust this resistor, the intensity adjustment 158 is set for a minimum output voltage and the internal adjustable resistor 140 is then adjusted so that the minimum output voltage obtained is that which is desired. By adjusting the resistor 140, the amount of the DC voltage applied to the base 144 of the transistor 146 is adjusted.

The continuously variable adjustment of the output voltage from the entire unit is controlled by means of the intensity control 158. This control can be adjusted by a dial placed on the front panel of the electrosurgical unit to obtain the output voltage desired. When the dial is varied in a clockwise rotation, it corresponds to an upward movement of the tap on the resistor 158 as seen in FIG. 3. This will increase the amount of current flowing through the resistor 160 and reduces the amount of current in the base 144 whereby the transistor 150 is not driven as hard, so that the screen voltage 166 on the oscillator 28 increases and the output voltage increases. When the dial is turned in a counterclockwise direction, it brings down the tap point on the resistor 158, as shown in FIG. 3. As the result, more current is caused to flow to the base 144 of the resistor and turns it on harder so that the transistor 150 is also turned on harder and pulls down more current through the transistor. As a result, the voltage on the screen 166 is lowered and the output voltage will be lowered.

It is therefore seen that a continuously variable output voltage is obtainable by means of a dial control, and it is adjusted so that clockwise rotation increases the output voltage, while counterclockwise voltage decreaes the output voltage. Changing of the adjustable intensity control 158 causes a change in the static operating point. However, the dynamic feedback still remains in the system.

The output is selected at a point along the tank circuit 34 which is appropriate for the system. The tank coil 34 actually provides an autotransformer action. As a result, the lower down the fixed point is set, the lower the source impedance becomes. However, the point cannot be placed too low since there is a desired output voltage that must be achievable. Therefore, the fixed point is a compromise between the maximum amount of voltage desired and the lowest source impedance obtainable. In fact, it is because of this low source impedance, combined with the dynamic low impedance due to the feedback circuit, which provides the substantially level voltage output regardless of load impedance.

Referring now to FIG. 5 there is shown a curve of the peak to peak output voltage as a function of the percent of dial rotation. The changing of the dial rotation causes an increases of the output voltage. Two curves are shown. A first curve 175 shows the open circuit output voltage without any load present. Curve 177 shows the same curve when a 1000 ohm load is placed across the output. It is noted that for at least 75% of the dial rotation, there is a very small percentage change in the output voltage. Inasmuch, as the vast majority of dental surgical procedures is conducted at intensities of between 450 and 600V *p-p*, the changes which occur at dial settings beyond 75% are not significant in actual practice. Further, tissue impedances encountered in dental applications are normally much higher than 1000 ohms which is used only as a standard factory test load.

This result can also be noted referring to FIG. 6 which shows a curve of peak to peak output voltage vs. peak to peak load current for different loads. For example, for a desired setting of approximately 500 volts, as the load is varied to draw a variation of output current from zero to 0.6 amps., the change in voltage is only approximately 25 volts. Such minimal change is contrasted with vast drops in the prior art. Because of the present system, the electrosurgical unit can keep the source impedance range of between 40–50 ohms, while the prior art would be approximately 300 ohms.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. An electrosurgical unit providing an output voltage to a load, comprising an oscillator producing an output signal of a given frequency, a control circuit means coupled to the oscillator for providing an output voltage from the oscillator for use in surgical procedures, a feedback circuit means coupled from the output to the input of the oscillator to maintain the output voltage level from the unit as a substantially constant value independent of the load, and wherein said oscillator includes a control electrode, and said control circuit means includes a switching transistor having its collector-emitter circuit connected between said control electrode and ground, and having a fixed voltage on its base, capacitor means, and means for selectively connecting said means to said base.

2. An electrosurgical unit as in claim 1, and wherein the oscillator includes a tank circuit for controlling the frequency of the output signal, the output voltage being extracted from said tank circuit, and wherein said feedback circuit means comprises sampling means coupled to the tank circuit for providing a sampled output signal as a signal proportional to the output voltage.

3. An electrosurgical unit as in claim 2, and wherein said sampling means further comprises a coil inductively coupled to said tank circuit for receiving an amount of said output voltage, and a detector circuit means for converting the amount received by said coil to a DC level, said DC level being said proportional signal.

4. An electrosurgical unit as in claim 3, and wherein said control circuit means further comprises an amplifier means having at least a control electrode and an output electrode the control electrode being connected to receive said DC level and the output electrode being connected to control said oscillator.

5. An electrosurgical unit as in claim 4, and wherein said amplifier means is a Darlington amplifier pair.

6. An electrosurgical unit as in claim 4, and further comprising a constant voltage source coupled to the control electrode of said amplifier means, and wherein said DC level is added to the output of said constant voltage source to provide the voltage level driving said amplifier means.

7. An electrosurgical unit as in claim 6, wherein said oscillator includes a grid circuit, and wherein said constant voltage source includes a Zener diode connected to the grid circuit and deriving its current from the self bias voltage developed in the oscillator grid circuit.

8. An electrosurgical unit as in claim 6, and further comprising intensity control means interconnected between said constant voltage source and said control electrode of said amplifier means for providing a selectable output voltage level over a range of continuously variable values from the unit, said DC level being supplied to said control electrode of said amplifier means in parallel with the output from said intensity control means.

9. An electrosurgical unit as in claim 4, and further comprising adjustable means interconnected between said control electrode of said amplifier means and said detector circuit means for providing an adjustment to correct for variations in the circuits.

10. An electrosurgical unit as in claim 4, and further comprising a reverse feedback means coupled between the output electrode and the control electrode of said amplifier means to maintain a desired voltage on said amplifier means.

11. An electrosurgical unit as in claim 10, and further comprising a stabilizing network means coupled to the output electrode of the amplifier means to prevent oscillation from the feedback loop.

12. An electrosurgical unit as in claim 1, and wherein said oscillator is a Clapp oscillator and wherein the input of the oscillator to which said feedback circuit means connects is the screen of the oscillator.

13. An electrosurgical unit as in claim 1, and wherein said selective connecting means further comprises a cutting switch means for connecting said capacitor means to said base to produce an unmodulated RF output and a coagulation switching means for removing said capacitor means from said base to produce a pulse modulated RF output and wherein said coagulation switching means and said cutting switch means are interconnected to prevent simultaneous operation thereof.

14. An electrosurgical unit as in claim 1, and further comprising power supply means for providing a fixed voltage supply and connected to energize said oscillator and said feedback circuit means.

15. An electrosurgical unit as in claim 1, and further comprising a handpiece unit coupled to the oscillator output for applying said output voltage level to a load, and a blocking circuit means connected across said handpiece unit for protecting said load from shocks due to starting transients.

16. An electrosurgical unit as in claim 15, and wherein said blocking circuit means includes a capacitor in series with the oscillator and handpiece unit, and a resistor in parallel with the oscillator and handpiece unit.

17. An electrosurgical unit as in claim 1, wherein said control electrode is a cathode electrode.

* * * * *